United States Patent [19]
Cox

[11] Patent Number: 5,885,210
[45] Date of Patent: Mar. 23, 1999

[54] SURGICAL RETRACTOR

[76] Inventor: Victor M. Cox, 5840 Zion Hill Dr., Lawndale, N.C. 28090

[21] Appl. No.: 157,978

[22] Filed: Sep. 21, 1998

[51] Int. Cl.⁶ .................................................. A61B 17/00
[52] U.S. Cl. ........................... 600/214; 600/219; 600/224
[58] Field of Search ................................... 600/201, 214, 600/219, 224, 226, 235

[56] References Cited

U.S. PATENT DOCUMENTS

| 579,625 | 3/1897 | Willbrandt . | |
|---|---|---|---|
| 1,018,868 | 2/1912 | Breneman . | |
| 1,500,227 | 7/1924 | Breneman . | |
| 5,681,265 | 10/1997 | Maeda et al. | 600/219 |

FOREIGN PATENT DOCUMENTS

| 135177 | 10/1933 | Austria | 600/224 |
|---|---|---|---|
| 1005345 | 4/1952 | France | 600/219 |
| 824663 | 12/1951 | Germany | 600/224 |

OTHER PUBLICATIONS

Grafstein, Paul et al., "Pictorial Handbook of Technical Devices", Chemical Publishing Co., Inc., New York, pp. 44–45, Item ak, 1971.

*Primary Examiner*—Jeffrey A. Smith

[57] ABSTRACT

A self-retaining hand-held surgical retractor includes a main pair of blades mounted to a pair of fulcrumed levers. The proximal ends of two longitudinally extending bars are mounted to a toggle link carried between the handles. The bars pass through arms projecting from the levers above the plane containing the levers. A pair of supplemental blades are mounted to the bars. Closing the handles directly causes both the main pair of blades and the supplemental pair of blades to recede from each other, and also causes the supplemental pair of blades to move rearwardly from the main pair of blades through the action of the toggle link.

9 Claims, 4 Drawing Sheets

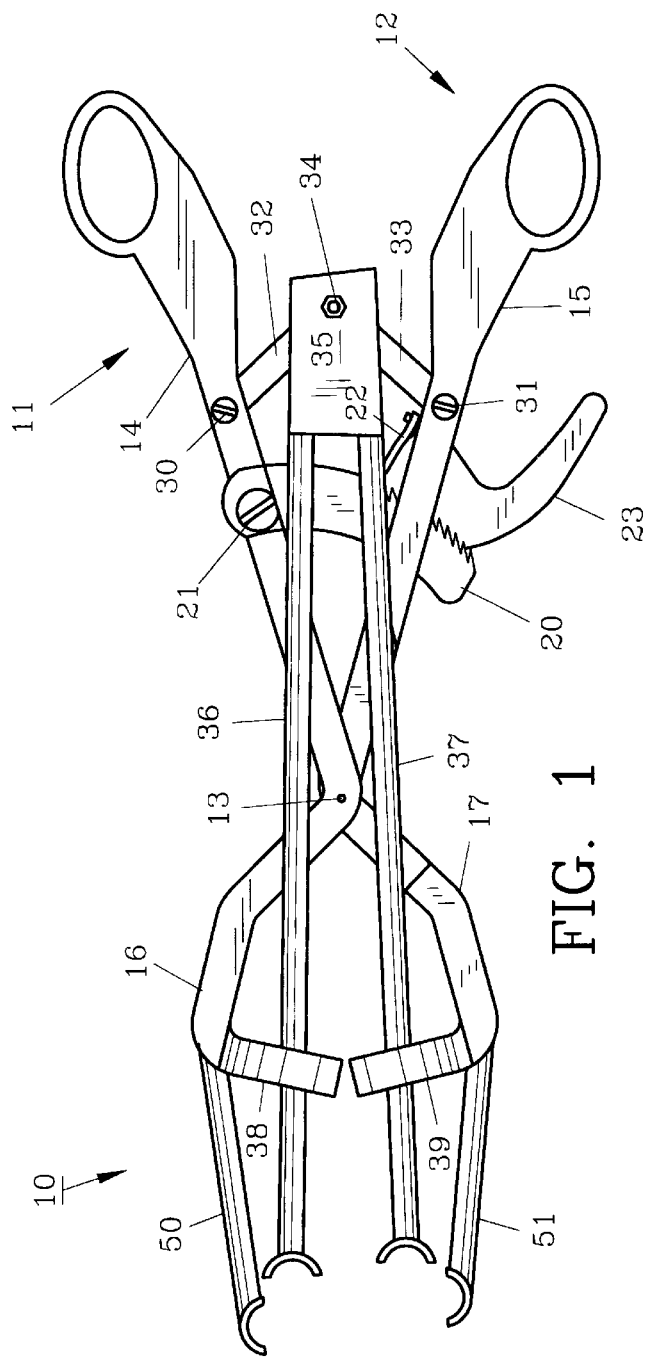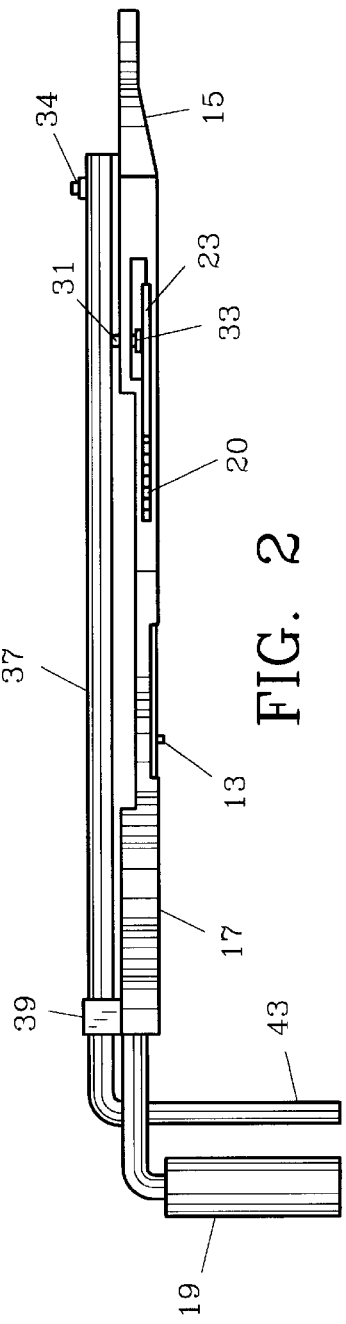

SURGICAL RETRACTOR

BACKGROUND OF THE INVENTION

This invention relates to surgical retractors, and more particularly pertains to a new and improved surgical retractor of the dilating type.

In commencing a surgical procedure, a general surgeon makes one or more incisions in a human body. In order to obtain unhindered access to underlying anatomical features, the surgeon then uses a retractor to dilate or reflect the skin or underlying layers of tissue. A typical retractor is formed from surgical steel and includes one or more smooth projections, called blades, which are mounted normal to the handle and retain an area of tissue adjacent to an incision. (The term "blade" is thus a term of art as used herein, because no sharp edge is required.) A simple retractor may include only a blade attached to a handle. If a blade is curved, it may be described as being a certain number of inches or millimeters deep and a certain number of inches or millimeters spread. The surface of a blade may be described as being either closed-end (solid) or open-end (open within the periphery). A finger-like blade may have either a blunt or pointed tip.

A conventional hand-held self-retaining dilating retractor features a pair of levers which are fulcrumed to each other between their ends. Each lever includes a rear end constituting a handle and a front end to which one or more blades are mounted. The pivot lies between each lever's front end and its rear end. As the handles are closed, the front ends spread apart, causing the blades to recede from each other. One handle carries a curved rachet and a thumb-operated pawl is pivotally mounted to the other handle.

One advantage of using such a retractor is that the user may use one hand to operate the retractor, freeing the other hand to perform other functions such as inserting sponges and the like. This convenience may allow a procedure to be performed using a smaller surgical staff, thereby reducing labor costs.

In the modem medical practice, a surgeon may perform the same type of procedure many times per day. Members of the surgical staff who would use a hand-held dilating retractor during procedures in which the length of the incision is relatively great and the forces exerted by the tissue upon the retractor are relatively large might suffer from fatigue and be subject to injury resulting from the necessity repeatedly to supply pressure to close the handles against a relatively high resistance of tissue until the pawl and rachet are engaged. A surgeon must consider these factors when deciding whether a hand-held dilating retractor is practical for use in certain procedures.

For these reasons, it is important that the retractor efficiently transmit force exerted by the user's hand to the blades. Limitations on conventional hand-held dilating retractors lead many surgeons to reject their use during certain procedures.

U.S. Pat. No. 1,018,868 disclosed a hand-held dilating speculum and retractor which included a pair of main levers each having a main blade and a pair of supplemental levers each having a supplemental blade. The pair of main levers were between the pair of supplemental levers, such that a side of each supplemental lever contacted a side of its adjacent main lever. The main levers were fulcrumed to each other by a countersunk rivet constituting a main pivot, so that as the handles of the main levers were moved toward each other (closed), the main blades receded from each other (opened). Each supplemental lever was fulcrumed to its adjacent main lever by a shouldered screw 3 extending through a longitudinally extending straight slot 4 in the supplemental lever and threaded in such main lever. Shouldered screws 3 were positioned slightly to the rearward of the main pivot. A pin 6 mounted to each main lever handle extended through a longitudinally extending straight longitudinal slot 5 in the handle of its adjacent supplemental lever. Thus, closing the handles of the main levers transmitted force through pins 6 to the handles of the supplemental levers, opening the pair of supplemental blades along with the pair of main blades. The facing surfaces of the supplemental lever handles were convexly curved, and a pin 8 mounted to each main lever handle projected a sufficient distance to extend alongside this convex surface of its adjacent supplemental lever handle. Closing the pair of main lever handles caused pins 8 to slide along the convex surfaces of the supplemental handles, thus causing the supplemental levers to move rearwardly with respect to the pair of main levers, such rearward motion guided by sliding of screws 3 in slots 4 and pins 6 in slots 5.

The device as above described was mechanically inefficient; the closing of the pair of main lever handles exerts transverse force to pins 8, which works well to open the blades but must be redirected to exert longitudinal force through the constraint of the convex surfaces. As much of the force exerted by pins 8 on the convex surfaces is normal to rather than parallel to the convex surfaces, friction is thereby generated between pins 8 and the convex surfaces. Friction also is generated by forces exerted by screws 3 normal to the surfaces forming slots 4. Thus, in order to obtain free movement of the device, it was necessary to employ a lubricant. The lubricant was difficult to keep sterile, and as the operative area was close to the lubricated surfaces, particularly those located on the supplemental lever handle facing the patient, there was danger of infection from this source. The inventor himself later described this device as being more or less impractical.

A subsequent device by the same inventor, disclosed in U.S. Pat. No. 1,500,227, enlarged the main lever handles and provided convexly curved slots therein, described as being cam slots, receiving pins extending from the respective adjacent supplemental lever handles. While this later device provided the convex surfaces at a location more to the rearward from the operative area to reduce the danger of infection, it remained more or less the same in terms of its mechanical inefficiency.

SUMMARY OF THE INVENTION

It is therefore an object of the present invention to provide a hand-held surgical retractor having a main pair of blades and a supplementary pair of blades, and which transmits force from the hand to the blades with greater efficiency.

Another object of the invention is to reduce fatigue and the risk of injury to surgeons and other surgical staff members who may be directed to use such retractors.

Still another object of the invention is to remove any surfaces generating friction farther to the rearward from the blades to further reduce any risk of infection.

Yet another object of the invention is to provide all of the benefits of prior art devices while removing entirely the supplemental fulcrumed levers, thereby removing the mechanical inefficiencies and high friction they caused.

Because the inventive retractor facilitates the use of an efficient hand-held device which may be useful in procedures involving large surface areas, such as abdominal procedures, and therefore which formerly may have been thought unsuitable for use with hand-held dilating retractors, the number of persons necessary in the operating theater may be reduced, advantageously reducing labor costs and increasing the convenience to the general surgeon.

These and other objects are provided by a hand-held dilating surgical retractor according to the invention.

The inventive retractor comprises a first lever and a second lever fulcrumed together between their ends at a main pivot. The main pivot lies between and delimits a front portion and a rear portion (handle) of each lever. A first retractor blade is mounted to said first lever front portion and a second retractor blade is mounted to said second lever front portion. These are referred to herein as the main pair of blades. The levers are shaped such that the first and second retractor blades recede from each other responsive to the closing of the handles, when the first lever rear portion approaches the second lever rear portion (when the handles are being closed).

Each lever front portion is provided with an arm whose proximal end is mounted thereto. The arms approach each other between the lever front portions.

A toggle joint is mounted between said first and second lever rear portions. The knee of the toggle joint is urged in a direction generally parallel to the levers responsive to closing of the handles.

First and second bars each are mounted at a proximal end thereof to a mount provided at the knee of the toggle joint. Each of the bars is slidably retained by an arm.

A third retractor blade is mounted to said first bar and a fourth retractor blade is mounted to the second bar. These blades will be referred to herein as the supplementary pair of blades. When the handles are closed, the supplementary pair of blades are pulled away from each other by the arms and are moved by the bars along with the knee. Typically, the knee is drawn rearwards towards the handle, but the invention also contemplates the use of a toggle joint in which the knee is pushed to the front as the handles are closed.

In order to avoid interference by the levers with the bars, it is recommended that the bars be carried out of the plane of said levers except where the bars are connected to the toggle joint. To help achieve this result, the distal end of each arm may be located out of a plane generally containing said levers. The bars preferably are located on the side of the device opposite to the blades, thus disposing the bars at a greater distance from the operative area.

During a surgical procedure, the surgeon or an assistant places the retractor on the surface of the body of the patient and inserts the four blades within the opening created by a body cavity, an incision, or wound. The handles are closed, opening a space between the four blades as the blades draw apart from each other. A conventional pawl and rachet self-retaining device may then be engaged, and the retractor then may be left to be supported on the body of the patient during the surgical procedure. At the conclusion of the procedure, the thumb then is used to disengage the pawl from the rachet to reopen the handles, thus bringing the blades back together and allowing the opening to close.

As described in *Gray's Anatomy*, the superficial fascia of the abdomen consists, over the greater part of the abdominal wall, of a single layer of fascia, which contains a variable amount of fat; but as this layer approaches the groin it is easily divisible into two layers, those being a superficial layer and a deeper layer, between which are found the superficial vessels and glands. The superficial layer is thick, and the deeper layer is thinner and more membranous in character than the superficial layer. In a second embodiment of a retractor according to the invention, the length of one blade may differ from the length of another blade, if such is desired to accommodate the differing depths of several layers of tissue to be retained.

BRIEF DESCRIPTION OF THE DRAWINGS

In order to facilitate a better understanding of the characteristics of the invention to those skilled in the art, a detailed description will be made on the basis of the accompanying drawings. Like numbers refer to like elements. The drawings are not necessarily drawn to scale.

FIG. 1 shows a plan view of a first embodiment according to the invention, the handles being open;

FIG. 2 shows a side elevation of the first embodiment;

DETAILED DESCRIPTION OF THE PREFERRED EMBODIMENTS

Figure 6:
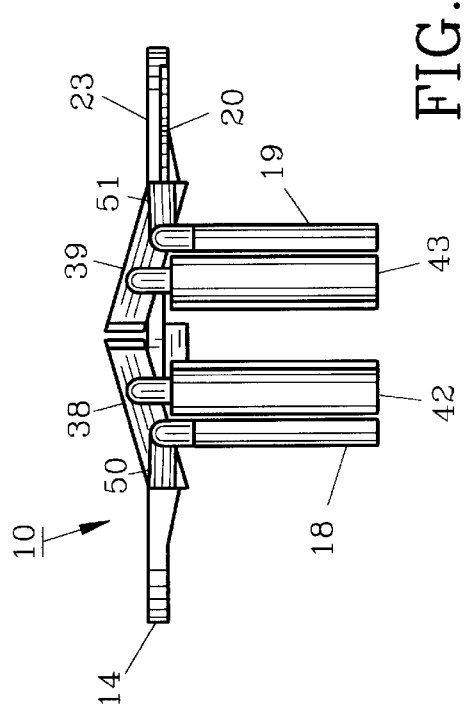
FIG. 6 shows a front elevation of the first embodiment.

A surgical retractor 10 according to the first preferred embodiment is shown in FIGS. 1 through 6. With reference to FIG. 1, retractor 10 conventionally includes first and second levers 11, 12 fulcrumed to each other at a main pivot 13, which may be a rivet, screw, or other suitable fastener. Forward of main pivot 13 are first lever front portion 16 and second lever front portion 17. With further reference to FIG. 6, first retractor blade 18 depends normal to leg 50 of first lever front portion 16, and second retractor blade 19 depends normal to leg 51 of second lever front portion 17. To the rearward of main pivot 13 are first lever rear portion 14 and second lever rear portion 15, herein called the first and second handles. For the convenience of the user, closed loop handles are formed in the lever rear portions 13, 14. The first lever 11 and second lever 12 are conventionally shaped such that as the handles approach each other (that is, as the handles are closed) first blade 18 and second blade 19 recede from each other in the transverse direction.

Also conventional is a self retaining mechanism. As the handles are closed, a spring pawl is moved against a ratchet so that the pawl engages the successive teeth of the ratchet to prevent any untimely reopening of the handles. Spring 22 bears against a cam-shaped surface of pawl 23, formed with a thumb-operated lever. Spring 22 and pawl 23 are mounted to second lever rear portion 15. Pawl 23 engages the teeth of rachet 20, which is mounted by fastener 21 to first lever rear portion 14.

A toggle link is disposed between the handles to convert a portion of the transversely directed force provided by the handles into the required longitudinally directed force. Toggles 32, 33 are mounted to and between the respective first and second handles 14, 15 by first and second toggle fasteners 30, 31. Toggles 32, 33 are pivoted at their distal ends by fasteners 30, 31 and each is also pivoted at its proximal end at a fulcrum screw 34 or other suitable fulcrum type fastener to form a knee.

Carried by knee 34 is a mount 35 to which the proximal ends of first and second bars 36, 37 are fastened. Mount 35 and bars 36, 37 are disposed on the side of retractor 10 opposite to the side to which the blades extend so as to keep the moving parts away from the body of the patient. With reference to FIGS. 1 and 6, first bar 36 extends through a hole in first arm 38, and second bar 37 extends through a hole in second arm 39. Third blade 42 depends from first arm 38 and fourth blade 43 depends from second arm 39.

Figure 4:
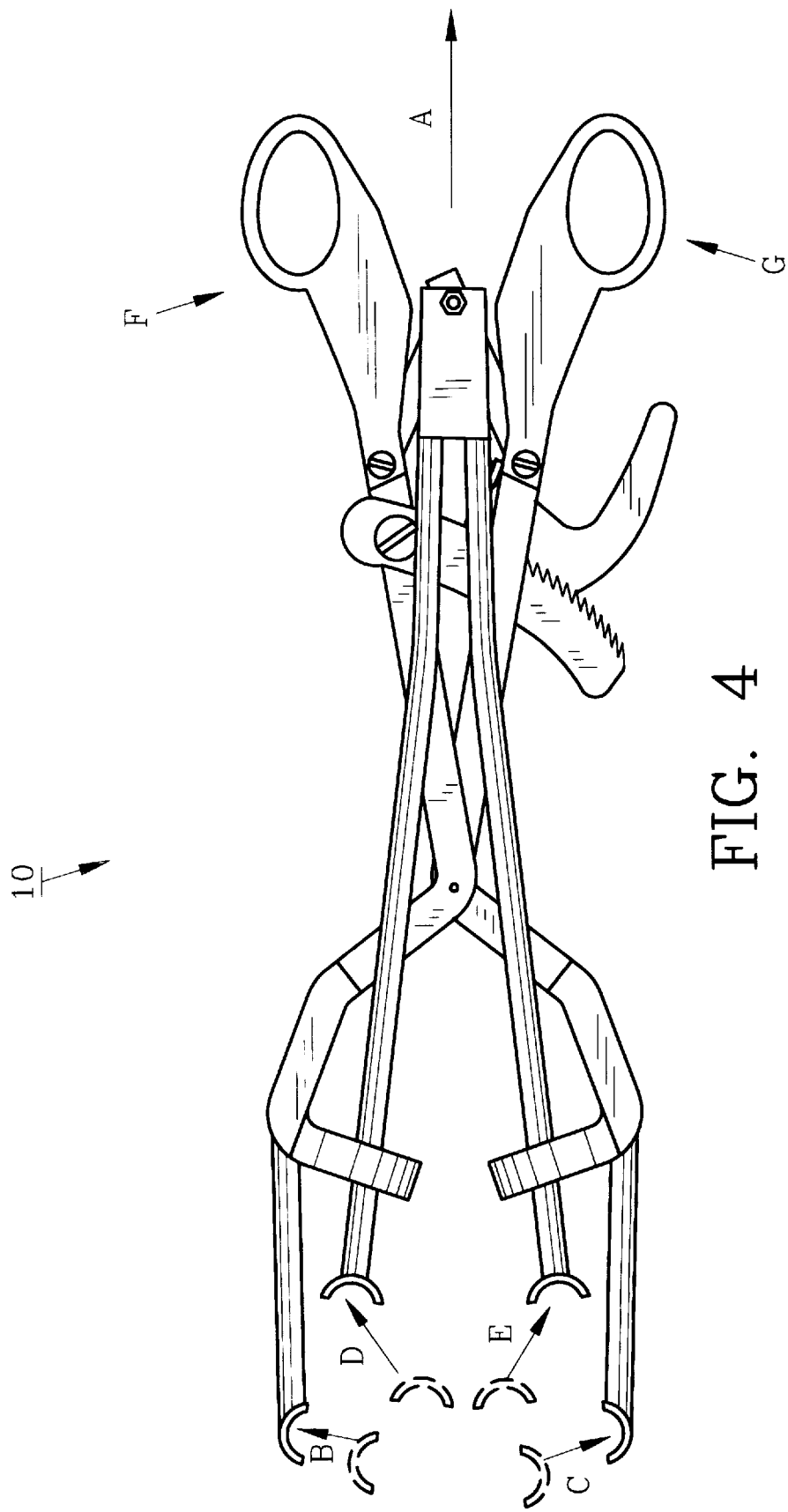
FIG. 4 shows the motions of components of the first embodiment as the handles are closed.
Figure 5:
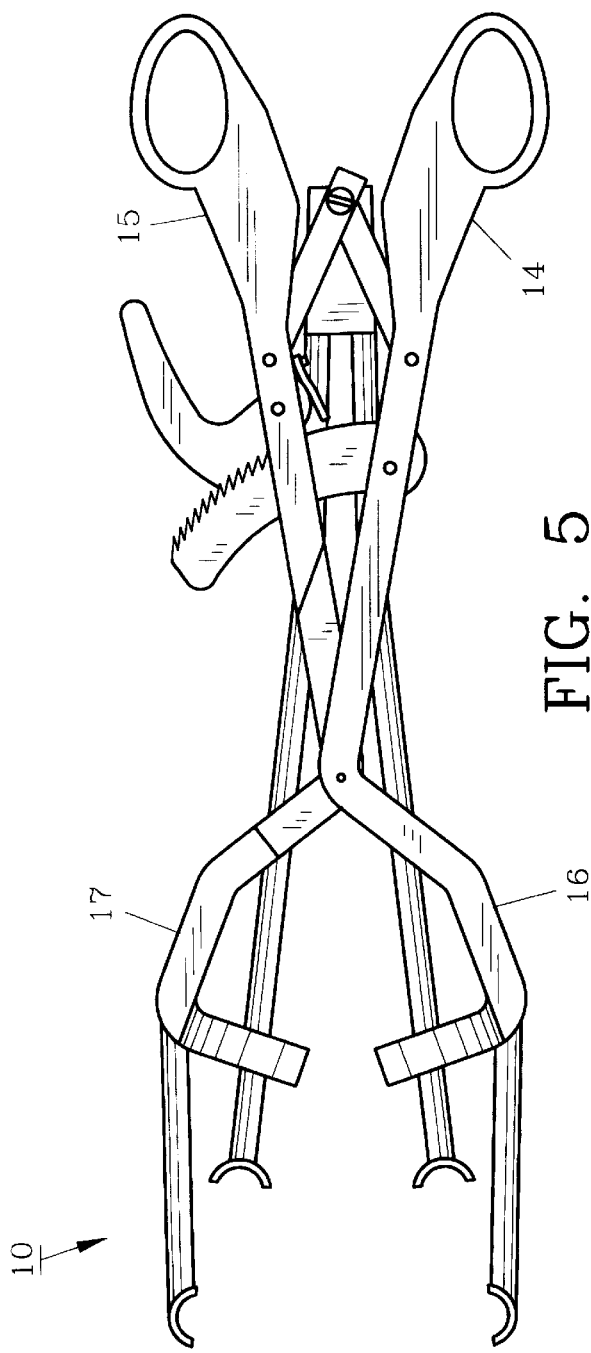
FIG. 5 shows the first embodiment as viewed from beneath, the handles being closed.

The handles are initially open and the blades are in a non-dilated position, as seen in FIGS. 1, 2, 3, and 6. Movements associated with operation of the retractor 10 is seen in FIG. 4. As the handles are closed (see arrows F and G), the first and second lever front portions 16 and 17 pivot about main pivot 13 to recede from each other in the transverse direction. Thus, first and second blades 18, 19 recede from each other in the transverse direction (see arrows B and C). As first and second arms 38, 39 also are mounted to front portions 16 and 17, the front portions of bars 36, 37 likewise recede from each other in the transverse direction. Thus, third and fourth blades 42, 43 recede from each other in the transverse direction (see transverse component of arrows D and E).

Closing of the handles also operates the toggle link, thereby drawing mount 35 rearward toward the closed loop handles (see arrow A). Mount 35 thereby draws rearward bars 36, 37 and third and fourth blades 42, 43 mounted thereto (see longitudinal component of arrows D, E).

Depending upon the materials used and the design, stress imparted by the pair of supplemental blades through the bars to the mount provides a slight opening force to the handles when the pawl is released from the ratchet as the stress is relieved.

Figure 3:
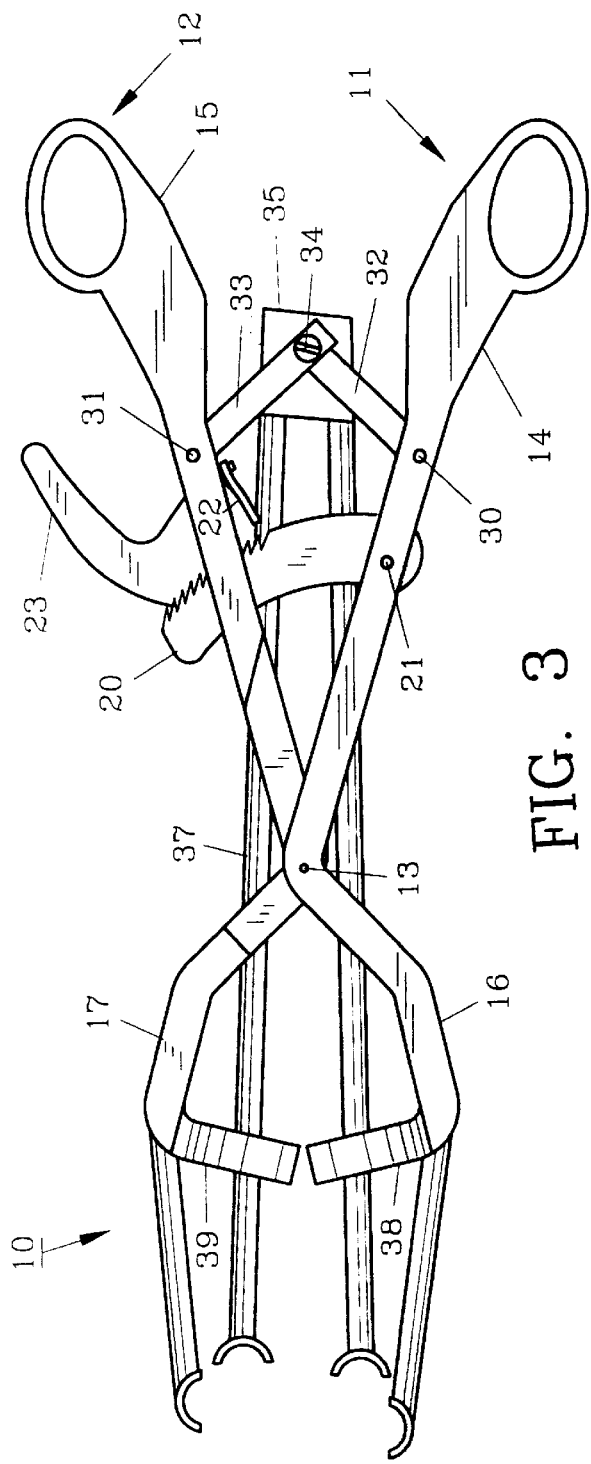
FIG. 3 shows the first embodiment as viewed from beneath, the handles being open.
Figure 7:
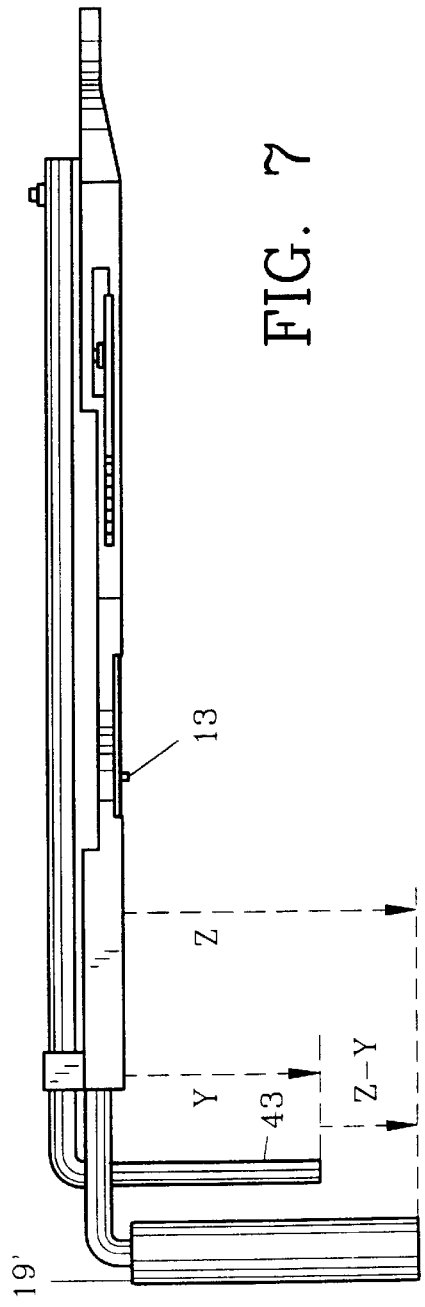
FIG. 7 shows a second embodiment according to the invention.

A retractor according to the second embodiment of the invention is shown in FIG. 7. In contrast to the view of the first embodiment of the invention as seen in FIG. 6, the device shown in FIG. 7 includes first and second blades 18', 19' (only blade 19' being visible from the side shown) which are longer than third and fourth blades 42, 43 relative to the plane in which the handles 14, 15 are disposed. As illustrated, blade 19' has a length Z and blade 43' has a length Y, Z being greater than Y by the distance (Z-Y) as so defined. A device according to the second embodiment may be used to accommodate the differing depths of several layers of tissue to be retained.

Retractors provided by the invention offer new advantages to the surgeon. Gone are the supplemental levers and the friction-generating structures necessary to bear against them to convert transverse motion to longitudinal motion. Transverse force to the supplemental blades is simply and efficiently provided in the transverse direction by arms 38, 39; as the device already has been designed to transmit transverse motion to the main pair of blades 18 and 19, no other structures are needed for transmission of transverse force. Longitudinal force is simply and effectively supplied by the toggle link in mechanical connection between a pair of handles and a plurality of blades. Because little or no transverse forces are applied to bars 36, 37, friction should not be a problem between bars 36, 37 and arms 38, 39, thereby removing any lubricant problem at the operative area. Any need for lubricant is minimal and limited to the toggle link, which is far removed from the operative area. Furthermore, the mass of the toggle link, bars 36 and 37, and arms 38, 39 is small compared to that needed for conventional supplementary levers. Furthermore, whereas one of the prior art supplementary levers was located on the side next to the patient, both bars of the inventive device are disposed opposite to the patient, minimizing or eliminating any problems associated with moving parts adjacent to the body surface. The overall simplicity and efficiency of retractors according to the invention allow them to be considered for operations previously thought unsuitable for the use of hand-held retractors.

Devices according to the invention are recommended to be made from surgical steel or other strong, fairly light, highly polished metal. The front lever portions 16, 17 may be made less thick in the area of the main pivot (see FIG. 2) to allow clearance for bars 36 and 37. While arms each having a hole therein are illustrated, any other guide which allows bars 36 and 37 to reciprocate may be used. The toggle link preferably is disposed between and equidistant from the handles with toggles 32 and 33 of equal length. The exact dimensions of an actual device depend upon the surgical procedure to be performed, and the relative positions of the blades with respect to each other in the open or closed positions may be varied according to the lengths and angles at which the several components are cast.

Since the invention may be embodied in several forms without departing from the spirit or essential characteristics thereof, the preceding description is intended to be illustrative and not restrictive, since the scope of the invention is defined by the claims rather than by the description preceding them.

What is claimed is:

1. A hand-held dilating surgical retractor, comprising:

a first lever and a second lever fulcrumed together between their ends at a main pivot, said main pivot being between a front portion and a rear portion of said first lever, and said main pivot likewise being between a front portion and a rear portion of said second lever;

a first retractor blade mounted to said first lever front portion and a second retractor blade mounted to said second lever front portion, said first and second levers being shaped such that said first and second retractor blades recede from each other responsive to the approach of said first lever rear portion to said second lever rear portion;

a first arm having a proximal end mounted to said first lever front portion and a second arm having a proximal end mounted to said second lever front portion, said first and second arms projecting toward each other;

a toggle joint mounted between said first and second lever rear portions, said toggle joint comprising a knee which is urged in a direction generally parallel to said levers responsive to the approach of said first lever rear portion to said second lever rear portion;

first and second bars each having a proximal end mounted to said toggle joint, said first bar being slidably retained by said first arm and said second bar being slidably retained by said second arm; and, a third retractor blade mounted to said first bar and a fourth retractor blade mounted to said second bar, whereby said third and fourth retractor blades are pulled away from each other by said arms and are moved by said bars along with said knee in response to the mutual approach of said first and second lever rear portions.

2. A hand-held dilating surgical retractor as set out in claim 1, further comprising a rachet-and pawl retainer mounted to said first and second lever rear portions.

3. A hand-held dilating surgical retractor as set out in claim 1, wherein the length of a blade relative to the plane in which the handles are disposed differs from the length of another blade with respect to said plane.

4. A hand-held dilating surgical retractor as set out in claim 1, wherein said knee is urged rearwardly with respect to said levers as said lever rear ends approach each other.

5. A hand-held dilating surgical retractor as set out in claim 1, wherein said arms each comprise a distal end located out of a plane generally containing said levers, said bars being carried out of the plane of said levers except at the toggle joint.

6. A hand-held dilating surgical retractor, comprising a toggle link in mechanical connection between a pair of handles and a plurality of blades.

7. A retractor as set out in claim 6, wherein said toggle link is disposed between and equidistant from said handles.

8. A retractor as set out in claim 6, further comprising bars connecting said toggle link and said plurality of blades.

9. A retractor as set out in claim 8, wherein said bars are substantially disposed on one side of the handles and the blades project to the other side of the handles.

\* \* \* \* \*